(12) United States Patent
Kelly

(10) Patent No.: US 11,648,371 B2
(45) Date of Patent: May 16, 2023

(54) SLEEP PATTERN OPTIMIZATION

(71) Applicant: Alan Kelly, Cambridge, MA (US)

(72) Inventor: Alan Kelly, Cambridge, MA (US)

( * ) Notice: Subject to any disclaimer, the term of this patent is extended or adjusted under 35 U.S.C. 154(b) by 972 days.

(21) Appl. No.: 16/514,583

(22) Filed: Jul. 17, 2019

(65) Prior Publication Data

US 2021/0016053 A1     Jan. 21, 2021

(51) Int. Cl.
| | | |
|---|---|---|
| *A61M 21/00* | (2006.01) | |
| *A61M 21/02* | (2006.01) | |
| *A61B 5/00* | (2006.01) | |
| *A61B 5/375* | (2021.01) | |
| *A61B 5/11* | (2006.01) | |

(52) U.S. Cl.
CPC ............. *A61M 21/02* (2013.01); *A61B 5/375* (2021.01); *A61B 5/4812* (2013.01); *A61B 5/1103* (2013.01); *A61B 5/4815* (2013.01); *A61B 5/4836* (2013.01); *A61B 5/6831* (2013.01); *A61M 2021/0027* (2013.01); *A61M 2021/0044* (2013.01); *A61M 2021/0066* (2013.01); *A61M 2021/0077* (2013.01)

(58) Field of Classification Search
CPC .................. A61M 21/00; A61M 21/02; A61M 2021/0005; A61M 2021/0016; A61M 2021/0022; A61M 2021/0027; A61M 2021/0044
See application file for complete search history.

(56) References Cited

U.S. PATENT DOCUMENTS

| | | | |
|---|---|---|---|
| 8,647,253 B2 * | 2/2014 | Iizuka .................. | B60K 28/066 600/26 |
| 9,474,876 B1 * | 10/2016 | Kahn ..................... | A61M 21/02 |
| 2015/0164409 A1 | 6/2015 | Benson et al. | |
| 2019/0224443 A1 * | 7/2019 | Jantunen ................ | G16H 20/70 |

* cited by examiner

*Primary Examiner* — John P Lacyk
(74) *Attorney, Agent, or Firm* — F. Chau & Associates, LLC

(57) ABSTRACT

Systems methods are described for modifying sleep patterns based on biofeedback. The method may include identifying a target sleep pattern from a plurality of candidate sleep patterns, receiving biofeedback information from a user, identifying a stimulus pattern based on the target sleep pattern and the biofeedback information, and providing at least one stimulus to the user based on the stimulus pattern.

20 Claims, 8 Drawing Sheets

SLEEP PATTERN OPTIMIZATION

CROSS-REFERENCE TO RELATED APPLICATIONS

This application claims priority to, and the benefit of, U.S. Provisional Application No. 62/786,415 filed on Dec. 29, 2018, entitled SYSTEM DESIGNED TO INFLUENCE SLEEP AND WAKING STATES BY AUTOMATICALLY RELEASING CANNABIS VAPOR BASED ON FEEDBACK FROM WEARABLE SENSOR SYSTEMS, as well as U.S. Provisional Application No. 62/719,871 filed on Aug. 20, 2018 entitled OPTIMAL STIMULI SYSTEM. The entire contents of the foregoing applications are hereby incorporated by reference for all purposes.

BACKGROUND

The following relates generally to modifying sleep patterns, and more specifically to modifying sleep patterns based on biofeedback.

Various types of noise producing systems, aromatherapy systems, and light (including 'natural light') systems may be used to induce a change in the state of a user. For instance, comforting noise systems like those that produce natural sounds similar to rain fall or a whale song are used to relax people during the day or to help a user sleep. Similarly, aromas (including gasses, vapors or smoke) are used in the field known as aromatherapy to induce certain states in users, for instance aromatherapies are commonly used in conjunction with massage to induce a relaxed state. Vapors or gasses that contain vaporized psychoactive and therapeutic chemicals, cannabinoids and medicines are commonly inhaled to create desired physical responses. Light, including artificially produced 'natural light' systems may be used in the treatment of medical disorders such as seasonal affective disorder. Furthermore, certain wavelengths of visible light have been shown to affect concentration, sleep states and anxiety.

In some examples, one or more stimulus may be provided to a user during sleep. However, the interaction of multiple stimuli on a user may be difficult to predict, and therefore may result in an undesirable effect on the user.

SUMMARY

Systems methods are described for modifying sleep patterns based on biofeedback. The method may include identifying a target sleep pattern from a plurality of candidate sleep patterns, receiving biofeedback information from a user, identifying a stimulus pattern based on the target sleep pattern and the biofeedback information, and providing at least one stimulus to the user based on the stimulus pattern.

The complex relationship between user characteristics, target improvements (i.e., cognitive or health improvements), and sleep patterns may be determined based on a machine learning model. The biofeedback information gathered from the user may be used to update and improve the machine learning model. The results of the machine learning model may be used to achieve the desired sleep patterns.

DETAILED DESCRIPTION

Embodiments of the present disclosure relate to systems and methods for improving sleep patterns using multiple stimuli. An example system produces a wide range of stimuli while also measuring the physical responses to those stimuli. The system may use sensors attached to the user to provide physiological response data to the stimuli creating system.

A prediction model such as a heuristic reinforcement-based algorithm, which may be located near the user or on a cloud-based server, may be used to learn what combinations of stimuli result in what autonomic and non-autonomic responses. For instance, example embodiments may create vapors using heated herbs or substances, aromas from the atomization of aromatherapy oils, sound from a speaker, and light from a light emitting diode (LED) system. These optimal periods may be based on data from the external sensors, such as peak rapid eye movement (REM) dream state measurements.

Embodiments of the present disclosure allow users to select a desired physical or cognitive response or improvement. The system learns what artificially produced stimuli increase the likelihood of achieving that physical response. Example embodiments use biofeedback with a controlled stimulus producing device to measure the direct physical response to a stimulus in order to increase the desired stimuli whilst reducing the undesired stimuli. As a result, the described systems and methods may reduce the time required to determine optimal sleeping or waking environment for the user (i.e., to achieve a target physical or cognitive improvement).

Example embodiments of the present disclosure directly measure the effect of the stimuli on a user. Example embodiments may also select stimuli based on directly measured biofeedback largely negating the need for the user to attempt to improve the system personally.

Example embodiments may be capable of maintaining sleep patterns associated with lucid dream states, or any other preferred state. In some embodiments, the release of cannabis vapor or other psychoactive substances may be combined with the release of light and sound patterns designed to enhance the effect of those stimuli.

Figure 1:
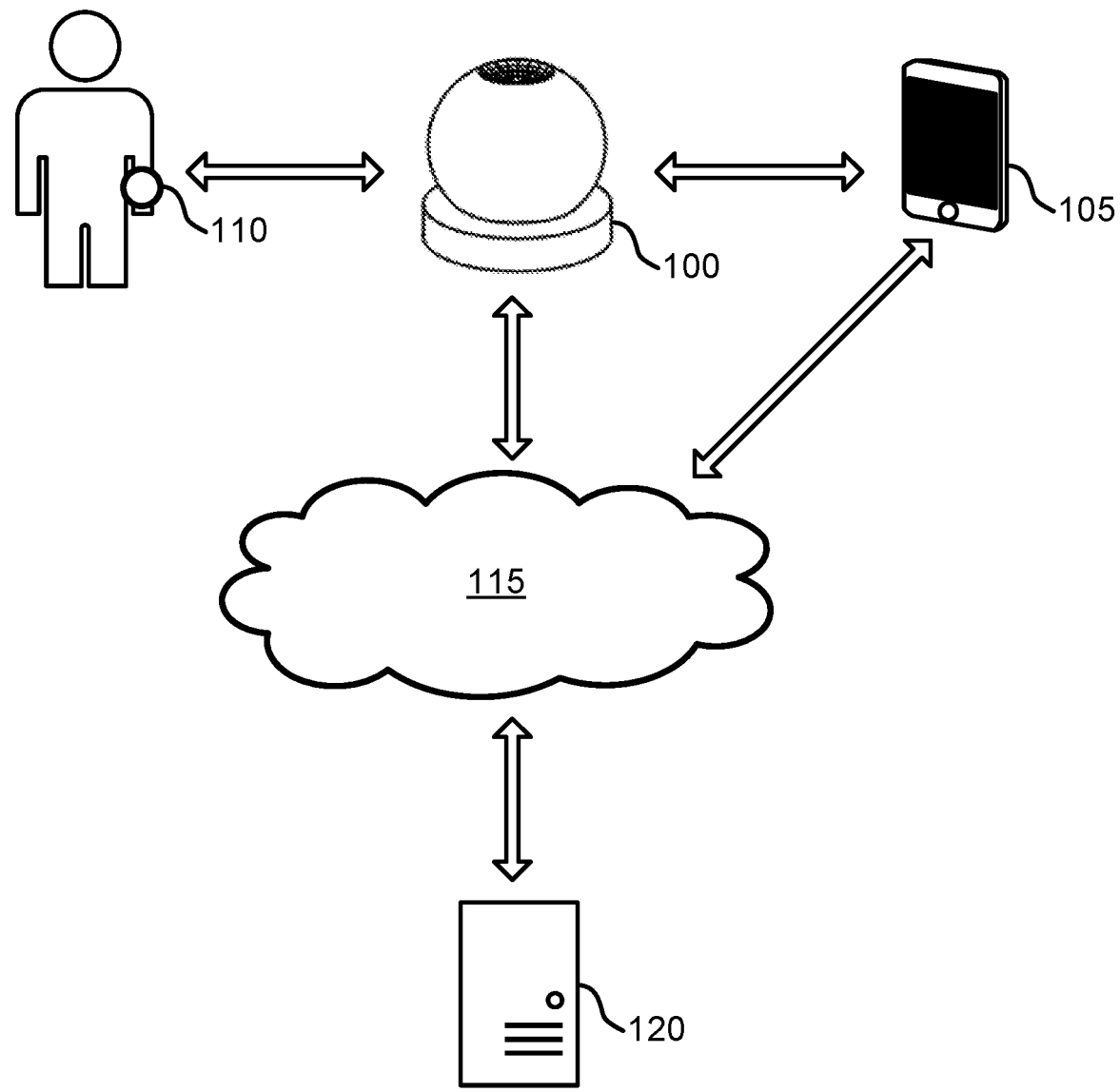
FIG. 1 shows an example of a sleep optimization system in accordance with aspects of the present disclosure.

FIG. 1 shows an example of a sleep optimization system in accordance with aspects of the present disclosure. The example shown includes sleep optimization device 100, mobile device 105, sensor 110, network 115, and server 120. Sleep optimization device 100 may be an example of, or include aspects of, the corresponding element or elements described with reference to FIGS. 2 and 3.

According to embodiments of the present disclosure, the sleep optimization system provides multiple stimuli (including sound, light, aromas, vapors, psychoactive substances, environmental conditions, etc.) via the sleep optimization device 100 to a user in order to achieve a target sleep pattern. The target sleep pattern may be selected based on data collected from the user (e.g., via mobile device 105). The sleep optimization device 100, the mobile device 105, or both may communicate with the server 120 via network 115 to identify the appropriate sleep pattern, and to identify the appropriate stimuli to provide the user in order to achieve that sleep pattern.

In an example embodiment, the sleep optimization system reads data from sensors 110, which may be attached to a user, to provide physiological response data (whether conscious or unconscious) to stimuli produced by the sleep optimization device 100. Data from the sensors 110 and stimuli share a common reference. Data from sensors and stimuli are compared to determine if a positive or negative physiological response are seen. If the feedback is positive (i.e., more of the users desired physiological responses are observed), the system will repeat that stimulus pattern to confirm that the stimulus patterns can produce the desired response. If confirmed, system may increase the amount, or positive or negative stimuli being produced. The cycle of providing stimulus, measuring feedback, and updating the stimulus may continue looping until a desired pattern of stimuli and environment are achieved. For example, the system may target a set of stimuli or environmental conditions that help the user achieve their desired physical state (i.e., longer sleep, better concentration, better memory or any other physiological target).

In example embodiments, the sleep optimization device 100 is tabletop unit (also referred to as a 'hub'.) Thus, the sleep optimization device 100 unit may be placed on a table or bedside unit. In other examples, the sleep optimization device 100 is integrated into the structure of a home or furniture or combined with another electronic device. In some examples, the sleep optimization device 100 may be integrated with, or may interact with a home assistant device.

In example embodiments, the sleep optimization device 100 produces a series of stimuli including but not limited to sound, light and aroma. These stimuli are generated in patterns determined by a digital control system powered by a local processing unit and may implement stimulus patterns (or 'experiments') uploaded to the processor from the server 120. These patterns may be random initially be random, or they may be based on reference data.

In some embodiments, the sleep optimization device 100 may include one or more processors. The one or more processors may include an intelligent hardware device, (e.g., a general-purpose processing component, a digital signal processor (DSP), a central processing unit (CPU), a graphics processing unit (GPU), a microcontroller, an application specific integrated circuit (ASIC), a field programmable gate array (FPGA), a programmable logic device, a discrete gate or transistor logic component, a discrete hardware component, or any combination thereof). In some cases, the processor may be configured to operate a memory array using a memory controller. In other cases, a memory controller may be integrated into processor. The processor may be configured to execute computer-readable instructions stored in a memory to perform various functions. In some examples, a processor may include special purpose components for modem processing, baseband processing, digital signal processing, or transmission processing. In some examples, the processor may comprise a system-on-a-chip.

The sensors 110 may include one or more devices capable of collecting biofeedback information. In one embodiment, the user wears the sensor 110. The sensor 110 may measure physiological metrics including, but not limited to, electroencephalogram (EEG) data, body temperature, heart rate, muscle tension, eye movement. These metrics may take the form of electrical activity, and may be amplified and converted for analysis within the sleep optimization device 100.

The mobile device 105 may be a mobile phone, a tablet, a personal computer, or any other suitable computing device capable of running a sleep optimization application and facilitating collection of input from a user. In some examples, the sleep optimization device 100 communicates with the mobile device 105 using a short range communications protocol such as Bluetooth, and the mobile device 105 may communicate with the server 120 via the network 115. In another example, the sleep optimization device 100 communicates with the server 120 directly (i.e., without passing the communications through the mobile device 105).

The server 120 may be a local or cloud-based system that records and reads data from the sensors set and correlates that data with stimuli produced via the hub. The server 120 determines patterns in the response data, and then seeks to confirm if those patterns are reproducible by performing experiments (i.e., producing stimuli and measuring the response).

The server 120 may include a machine learning model to generate target improvements, sleep patterns and stimulus patterns (i.e., the 'experiments). For example, server 120 may include one or more machine learning models such as an artificial neural network (ANN). An ANN may be a hardware or a software component that includes a number of connected nodes (a.k.a., artificial neurons), which may be seen as loosely corresponding to the neurons in a human brain. Each connection, or edge, may transmit a signal from one node to another (like the physical synapses in a brain). When a node receives a signal, it can process the signal and then transmit the processed signal to other connected nodes. In some cases, the signals between nodes comprise real numbers, and the output of each node may be computed by a function of the sum of its inputs. Each node and edge may be associated with one or more node weights that determine how the signal is processed and transmitted.

During the training process, these weights may be adjusted to improve the accuracy of the result (i.e., by minimizing a loss function which corresponds in some way to the difference between the current result and the target result). The weight of an edge may increase or decrease the strength of the signal transmitted between nodes. In some cases, nodes may have a threshold below which a signal is not transmitted at all. The nodes may also be aggregated into layers. Different layers may perform different transformations on their inputs. The initial layer may be known as the input layer and the last layer may be known as the output layer. In some cases, signals may traverse certain layers multiple times. In some embodiments, an ANN (or another machine learning model) on the server 120 may be trained using data from stimulus patterns provided via the sleep optimization device 100, mobile device 105 and biofeedback from the sensors 110.

Server 120 may provide one or more functions to requesting users linked by way of one or more of the various networks. In some cases, the server 120 may include a microprocessor board, which may include a microprocessor responsible for controlling all aspects of the server. In some cases, a server 120 may use microprocessor and protocols to exchange data with other devices/users on one or more of the networks via hypertext transfer protocol (HTTP), and simple mail transfer protocol (SMTP), although other protocols such as file transfer protocol (FTP), and simple network management protocol (SNMP). In some cases, a server 120 may be configured to send and receive hypertext markup language (HTML) formatted files (e.g., for displaying web pages). A server 120 may be a general purpose computing device, a personal computer, a laptop computer, a mainframe computer, a supercomputer, or any other suitable processing apparatus. In some examples, server 120 may be a combination of logical functions that operate in a "serverless" architecture.

Server 120 may receive the cognitive performance information from a local unit (i.e., sleep optimization device 100 or mobile device 105). Server 120 may also input the cognitive performance information to a machine learning model, where the response is based on a prediction of the machine learning model. Server 120 may then update the machine learning model based on a result of the subsequent cognitive test. Server 120 may also receive the target cognitive improvement from a local unit. Server 120 may input the target cognitive improvement to a machine learning model, where the response is based on a prediction of the machine learning model. Server 120 may also receive the biofeedback information from a local unit. Server 120 may input the biofeedback information to a machine learning model, where the response is based on a prediction of the machine learning model. Server 120 may then update the machine learning model based on the biofeedback information.

Figure 2:
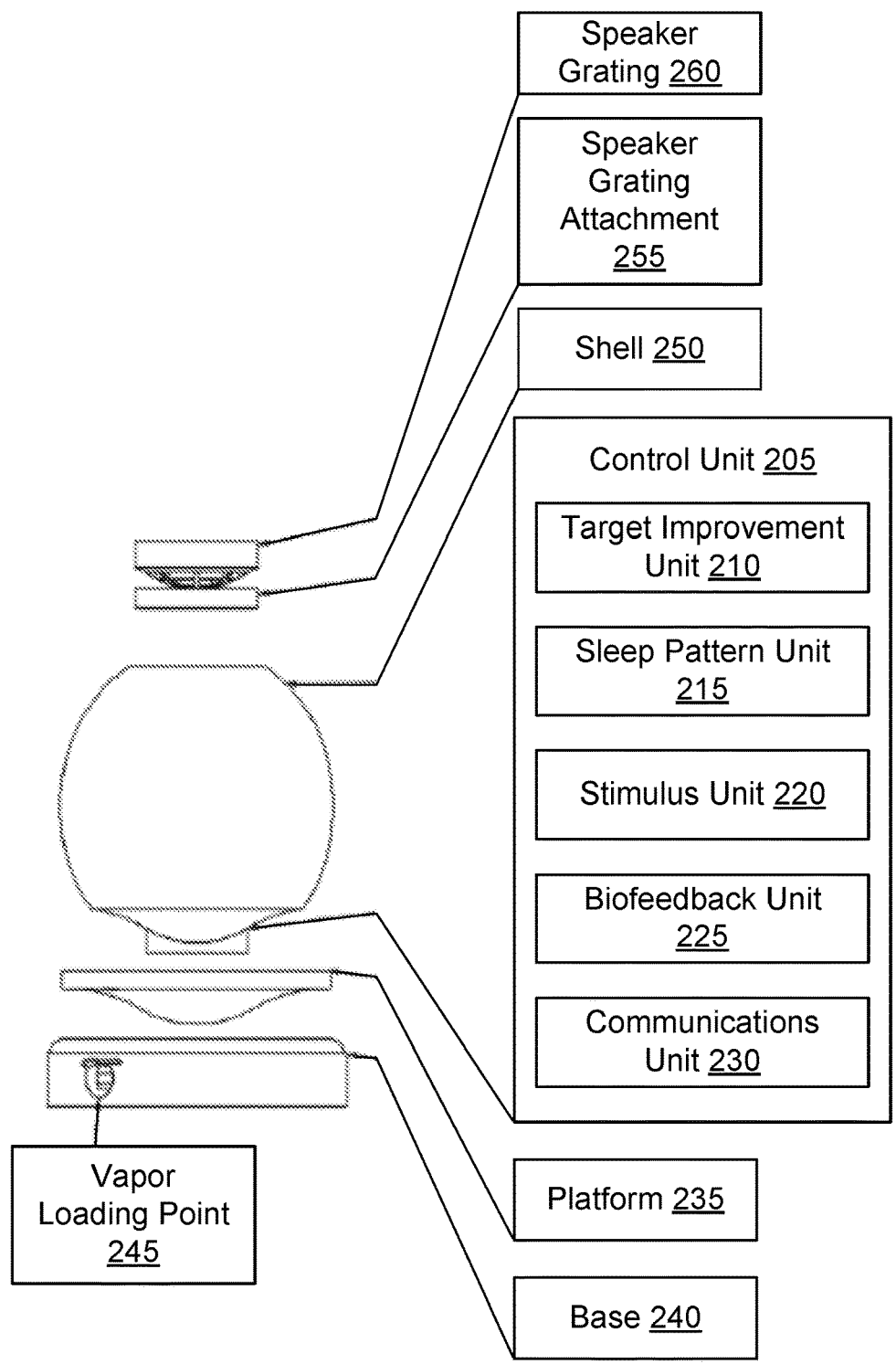
FIGS. 2 through 3 show examples of a sleep optimization device in accordance with aspects of the present disclosure.

FIG. 2 shows an example of a sleep optimization device 200 in accordance with aspects of the present disclosure. Sleep optimization device 200 may be an example of, or include aspects of, the corresponding element or elements described with reference to FIGS. 1 and 3. Sleep optimization device 200 may include control unit 205, platform 235, base 240, vapor loading point 245, shell 250, speaker grating 255, and speaker grating 260.

In one embodiment, sleep optimization device 200 comprises a bedside unit that produces light (e.g., via internal LEDs), sound (e.g., via a digital speaker system) and aroma or vapor (e.g., using a vaporizer-based system). In some cases, the sleep optimization device 200 will produce these stimuli in a randomized fashion as the user begins to sleep. In this embodiment the user will wear a sensor set (which may include an elasticated band that contains a plurality of sensors). For example, the sensor set may include EEG sensors, muscle tension sensors, temperature sensors and eye movement sensors. The sensors may be powered a local power source contained in the headset.

Data from the sensors may be transmitted via Bluetooth or WIFI to the sleep optimization device 200. The sleep optimization device 200 records the data from the sensors and correlates the data with local and/or system time. The sleep optimization device 200 also records the stimulus patterns produced each time. The sleep optimization device 200 may upload the data to a server (either directly or via a user's mobile device). The data will then be used by the cloud-based learning system for analysis of the stimulus patterns and biofeedback. The cloud based system may uses deep reinforcement learning based system to determine links between the stimuli and response. Thus, the cloud-based system or the sleep optimization device 200 may determine a new pattern of stimuli based on the biofeedback. This feedback loop may continue until a desired sleep state is achieved.

Control unit 205 may include target improvement unit 210, sleep pattern unit 215, stimulus unit 220, biofeedback unit 225, and communications unit 230. In some embodiments, components depicted as being a part of the sleep optimization device 200 may also be located on user's mobile device or on a remote server. For example, the target improvement unit 210, sleep pattern unit 215, or biofeedback unit 225 may be located on a mobile device or a remote server.

Target improvement unit 210 may identify a target cognitive improvement. Target improvement unit 210 may also provide a cognitive test to the user. Target improvement unit 210 may also receive cognitive performance information based on the cognitive test, where the target cognitive improvement is based on the cognitive performance information. Target improvement unit 210 may also provide a cognitive performance target recommendation to the user based on the cognitive performance information. Target improvement unit 210 may also provide subsequent cognitive tests to the user (i.e., to measure the impact of the sleep optimization interventions, or to select a new target improvement).

In some examples, target improvement unit 210 may receive a cognitive improvement selection from the user, where the target cognitive improvement is based on the cognitive improvement selection. In some examples, the target cognitive improvement includes a memory target, a concentration target, an energy target, an anxiety reduction target, a problem solving ability target, or any combination thereof. In some examples, the target cognitive improvement includes a waking cognitive performance improvement target. Target improvement unit 210 may also identify a target health improvement. Target improvement unit 210 may also provide a health survey to the user, where the target health improvement is based on the health survey.

Sleep pattern unit 215 may identify a target sleep pattern from a set of candidate sleep patterns. For example, the set of candidate sleep patterns may be represented by parameters for setting the time period of various sleep stages. Sleep pattern unit 215 may also select the target sleep pattern based on the target cognitive improvement. Sleep pattern unit 215 may also select the target sleep pattern based on the target health improvement. Sleep pattern unit 215 may also identify one or more user characteristics, where the target sleep pattern is identified based on the one or more user characteristics. In some examples, the one or more user characteristics include an age, a gender, health information, a sleep history, or any combination thereof.

Sleep pattern unit 215 may also provide a survey to the user (i.e., via an application on the user's mobile device), where the one or more user characteristics are based on the survey. In some examples, the target sleep pattern includes a sleep pattern associated with a lucid dream state. Sleep pattern unit 215 may also identify a subsequent user activity, where the target sleep pattern is based on the subsequent user activity. For example, if the user indicates that they have an important work presentation coming up, an appropriate cognitive target may be selected, whereas a different target may be selected if a weekend or vacation is approaching).

In some examples, the target sleep pattern includes a set of target sleep stages, where each of the target sleep stages is associated with one or more time intervals. In some examples, the set of sleep stages includes a rapid eye movement (REM) stage, a non-REM stage, an N1 sleep stage, and N2 sleep stage, an N3 sleep stage, or any combination thereof.

Stimulus unit 220 may identify a stimulus pattern based on the target sleep pattern and the biofeedback information. Stimulus unit 220 may also provide at least one stimulus to the user based on the stimulus pattern. In some examples, the at least one stimulus is selected from a set of stimuli including sounds, lights, vapors, aromas, or any combination thereof. In some examples, the at least one stimulus includes at least two stimuli from the set of stimuli. In some examples, the set of stimuli further includes a haptic stimulus, a temperature stimulus, a pain stimulus, a taste stimulus or any combination thereof. Stimulus unit 220 may also provide a sleep initiation stimulus to the user. Stimulus unit 220 may also provide a waking stimulus to the user.

Biofeedback unit 225 may receive biofeedback information from a user (i.e., from sensor 105). In some examples, the biofeedback information includes electroencephalogram (EEG) information, electrocardiogram (ECG) information, electromyogram (EMG) information, mechanomyogram (MMG) information, electrooculography (EOG) information, galvanic skin response (GSR) information, magnetoencephalogram (MEG) information, pulse information, breathing information, or any combination thereof. In some examples, the biofeedback and the at least one stimulus are provided as part of a continuous feedback loop.

Communications unit 230 may transmit the cognitive performance information to a cloud based server. Communications unit 230 may also receive a response from the cloud based server, where the target cognitive improvement is based on the response. Communications unit 230 may also transmit the target cognitive improvement to a cloud based server. Communications unit 230 may also receive a response from the cloud based server, where the target sleep pattern is based on the response. Communications unit 230 may also transmit the biofeedback information to a cloud based server. Communications unit 230 may also receive a response from the cloud based server, where the stimulus pattern is based on the response.

Figure 3:
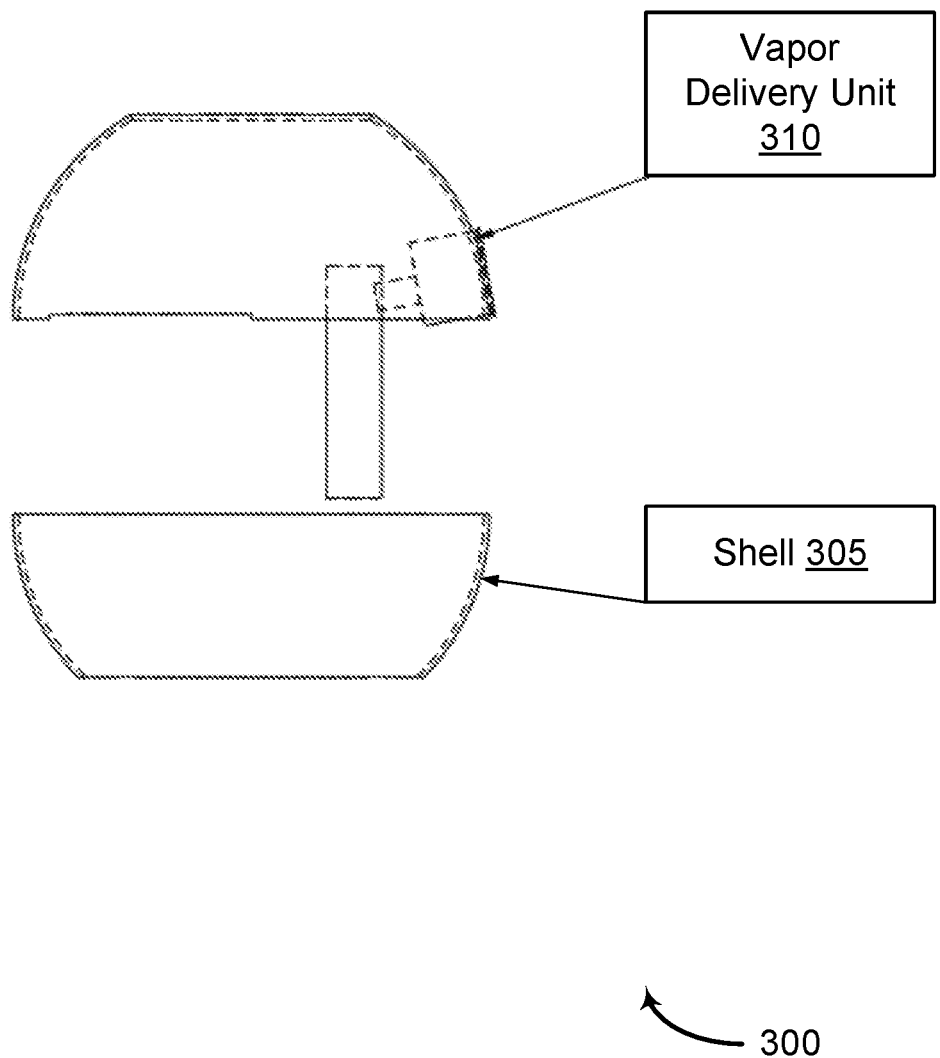

FIG. 3 shows an example of a sleep optimization device 300 in accordance with aspects of the present disclosure. Sleep optimization device 300 may be an example of, or include aspects of, the corresponding element or elements described with reference to FIGS. 1 and 2. Sleep optimization device 300 may include shell 305 and vapor delivery unit 310.

Example embodiments of the present disclosure provide for vaporizing the active chemical elements in cannabis or other psychoactive substances, thereby allowing a user to inhale said vapor. In some cases, a vapor delivery unit 310 may be provided which may eject the vapor at an angle (which may be configurable by the user) so a desired amount of vapor may be inhaled by the user.

Cannabis vapors or other vapors may be used to induce physiological change in a user. For example, vapors may be used to reduce pain or anxiety and have multiple other uses depending on the marijuana strain and active element inhaled. The sleep optimization device 300 may produce vapor based on measured physiological states of the user, thus responding directly to the users' needs in a quantifiable manner which may be otherwise immeasurable or undetectable to the user.

For example, a user may inhale vapors to reduce anxiety once the user is experiencing a full-blown panic attack. The sleep optimization device 300 may use physiological measures from a sensor attached to the user to predict an upcoming panic attack and then determine the optimal time to release a vapor to counter the effect before the user experiences it. In some examples, the sleep optimization device 300 may be used for non-human (i.e., animal) to create stimuli (including vapors) based on biofeedback (e.g., from in vivo or invitro sensor units). This data may be analyzed (e.g., at a cloud based server), and additional stimuli may be generated based on the analysis.

The sleep optimization device 300 may be used to achieve both waking and sleep states. For users who desire to prolong deep sleep, the sleep optimization device 300 will determine the relationship between stimulus (i.e., vapor dosage) and sleep and learn to produce the desired amount at the correct time to positively effect that state. In another instance the user may wish to experiment with the induction of a lucid dream. Lucid dreaming enthusiasts may use stimuli in the form of sound and light to induced lucid dreams. The sleep optimization device 300 may enable the use of a psychoactive vapors at key points in the REM sleep cycle to induce or sustain lucid dreams.

Figure 4:
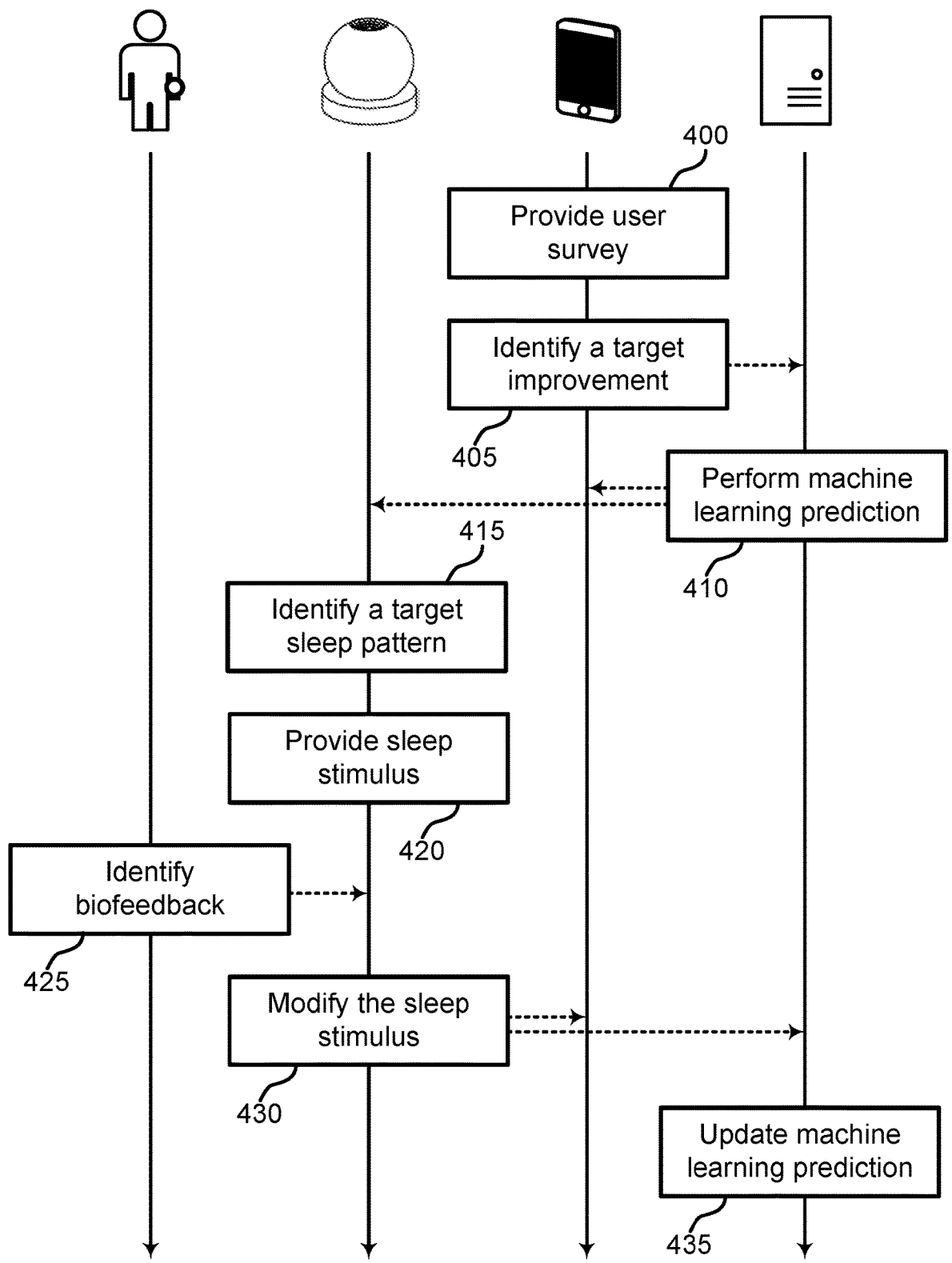
FIGS. 4 through 8 show examples of a process for modifying sleep patterns based on biofeedback in accordance with aspects of the present disclosure.

FIG. 4 shows an example of a process for modifying sleep patterns based on biofeedback in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

The devices performing each step illustrated in FIG. 4 are provided as examples, and are not limiting of the present disclosure. Thus, for example, steps shown as being performed by a sleep optimization device may also be performed at the user's mobile device (or vice versa).

At step 400, the system may provide a user survey. For example, the user may provide profile information or take a cognitive test to determine opportunities for improving cognitive functioning (e.g., improved memory, improved concentration, reduced anxiety, improved problem solving ability, etc.). In some examples, the survey may be in the form of a game designed to measure cognitive performance. Subsequent cognitive surveys, tests or games may be provided to measure the impact of the sleep optimization functions, and the data may be used to train a machine learning model, which can then be used to appropriately select more effective sleep patterns and stimulus patterns.

At step 405, the system may identify a target improvement. In some cases, the user selects the target improvement. In other examples a target improvement is suggested to the user. In some examples, a machine learning model may be used at a cloud based server to predict an appropriate target improvement. Steps 400 and 405 may be performed via the mobile device. In some cases the target improvement is a cognitive functioning improvement. In other examples, the target improvement may be a health improvement, a sleep improvement, an enjoyable experience, or a relaxation target.

At step 410, the system may perform machine learning prediction (e.g. at a cloud based server) to identify a target sleep pattern, a stimulus pattern, or both. In some examples, one or both of the target sleep pattern or the stimulus pattern are identified at the local sleep optimization device (or via an application on the user's mobile device).

At step 415, the system may identify a target sleep pattern. In some cases, step 415 may be performed on a cloud based server, or it may be performed at the local sleep optimization device.

At step 420, the system may provide sleep stimulus. Stimuli may be produced according to a pattern that includes light, sound, heat, vapor, or other environmental stimuli. In some examples, the stimuli may be provided as part of an 'experiment' which may be used to gather data for training a machine learning model that can predict the impact of various combinations of stimuli at different points of a sleep cycle.

At step 425, the system may identify biofeedback information. For example, the system may gather biofeedback from sensors located on or near the user. In some examples, the biofeedback information is passed to the server, which produces an updated stimulus pattern designed to achieve the desired sleep state according to the identified sleep pattern.

At step 430, the system may modify the sleep stimulus based on the biofeedback information. In some cases, during an initial training period, randomized stimuli may be provided to assist in training a machine learning model. Then, when the system determines that stimuli can be provided to achieve a desired physiological effect with a threshold degree of confidence, the randomization may be reduced, and the stimulus pattern may comprise a set of stimuli designed to accurately manipulate a state of the user (either sleeping or awake).

At step 435, the system may update a machine learning model or prediction based on the biofeedback information. In other words, the stimulus, the biofeedback information, and the model predictions may be connected in a loop so that the operation of the sleep optimization device may be continuously improved.

Figure 5:
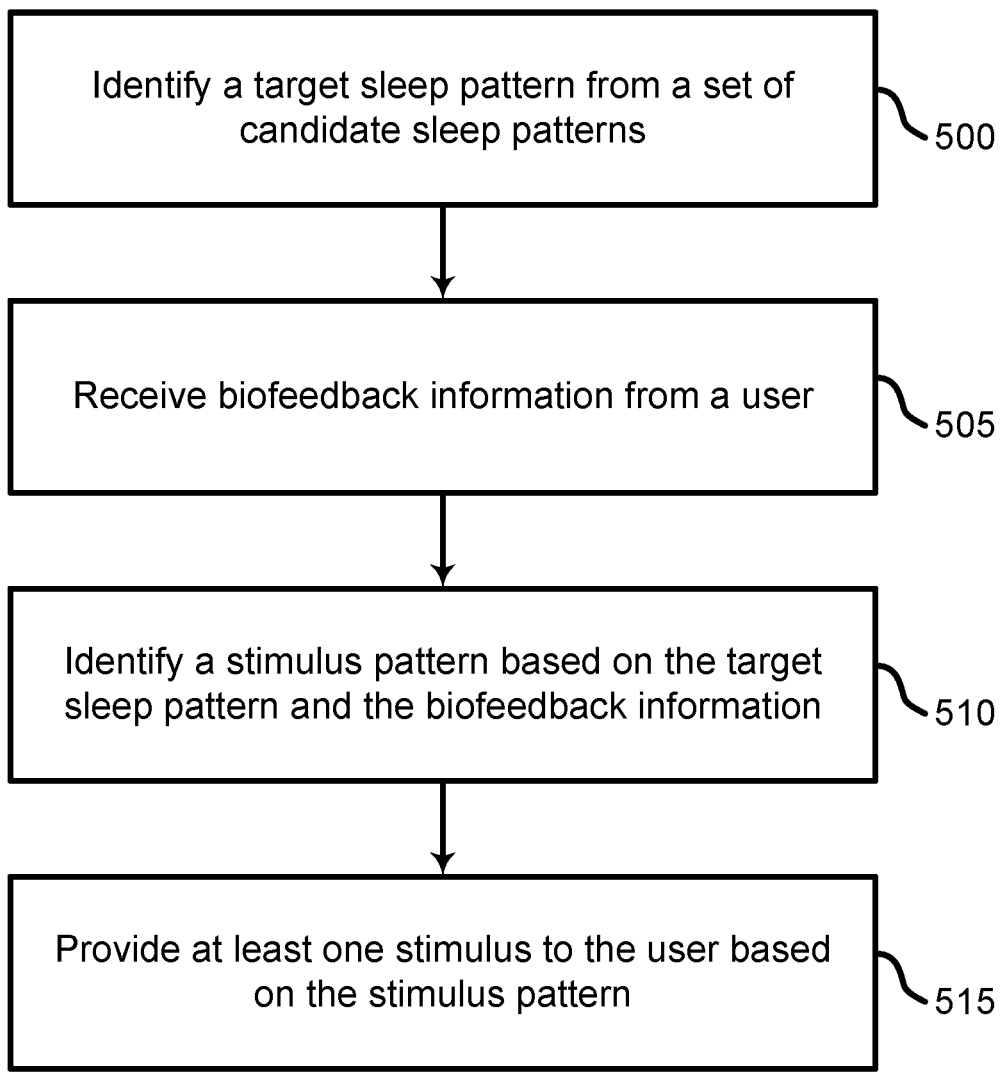

FIG. 5 shows an example of a process for modifying sleep patterns based on biofeedback in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

At step 500, the system may identify a target sleep pattern from a set of candidate sleep patterns. In some cases, the operations of this step may refer to, or be performed by, a sleep pattern unit as described with reference to FIG. 2.

At step 505, the system may receive biofeedback information from a user. In some cases, the operations of this step may refer to, or be performed by, a biofeedback unit as described with reference to FIG. 2.

At step 510, the system may identify a stimulus pattern based on the target sleep pattern and the biofeedback information. In some cases, the operations of this step may refer to, or be performed by, a stimulus unit as described with reference to FIG. 2.

At step 515, the system may provide at least one stimulus to the user based on the stimulus pattern. In some cases, the operations of this step may refer to, or be performed by, a stimulus unit as described with reference to FIG. 2.

Figure 6:
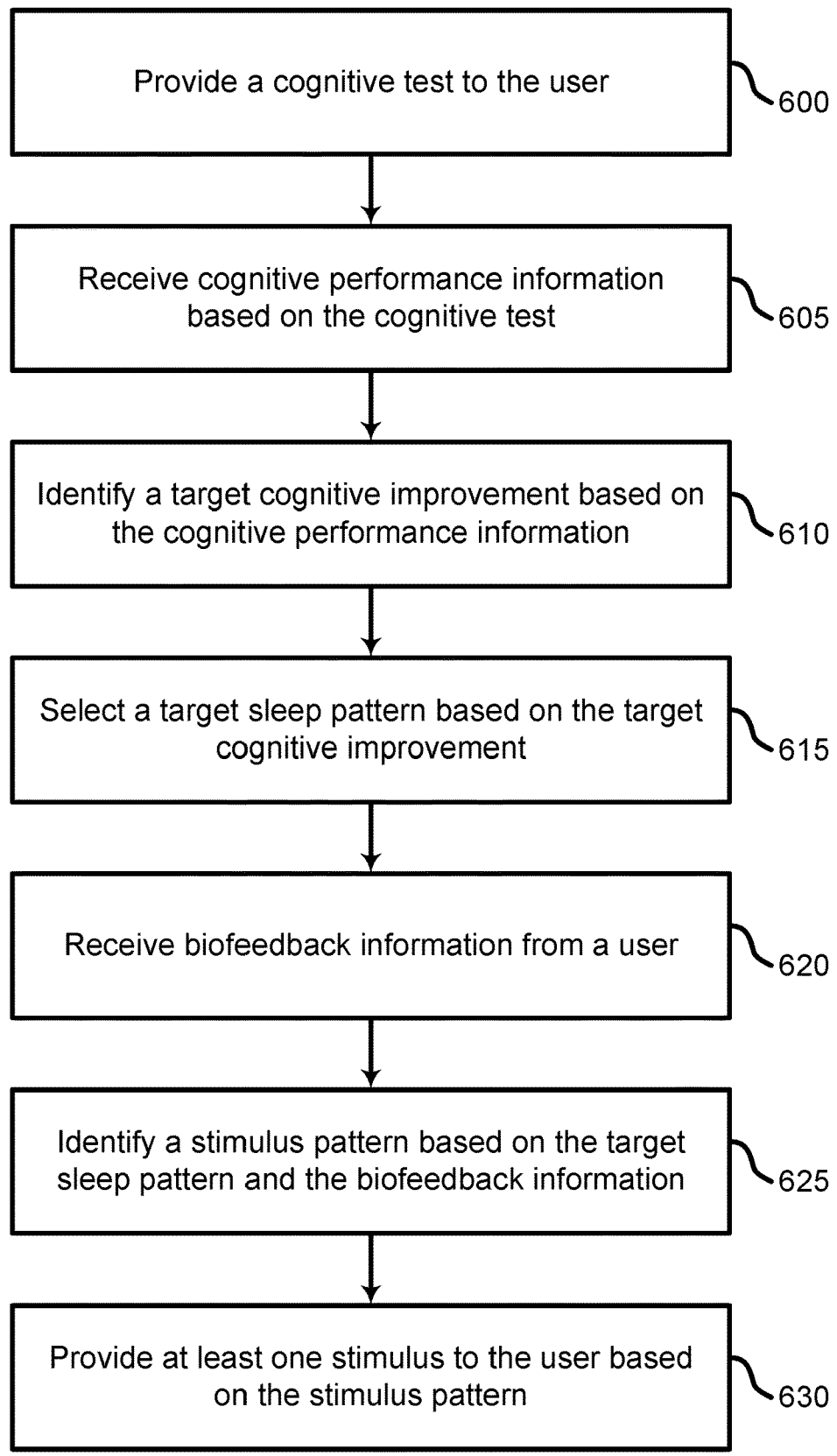

FIG. 6 shows an example of a process for modifying sleep patterns based on biofeedback in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

At step 600, the system may provide a cognitive test to the user. In some cases, the operations of this step may refer to, or be performed by, a target improvement unit as described with reference to FIG. 2.

At step 605, the system may receive cognitive performance information based on the cognitive test. In some cases, the operations of this step may refer to, or be performed by, a target improvement unit as described with reference to FIG. 2.

At step 610, the system may identify a target cognitive improvement based on the cognitive performance information. In some cases, the operations of this step may refer to, or be performed by, a target improvement unit as described with reference to FIG. 2.

At step 615, the system may select a target sleep pattern based on the target cognitive improvement. In some cases, the operations of this step may refer to, or be performed by, a sleep pattern unit as described with reference to FIG. 2.

At step 620, the system may receive biofeedback information from a user. In some cases, the operations of this step may refer to, or be performed by, a biofeedback unit as described with reference to FIG. 2.

At step 625, the system may identify a stimulus pattern based on the target sleep pattern and the biofeedback information. In some cases, the operations of this step may refer to, or be performed by, a stimulus unit as described with reference to FIG. 2.

At step 630, the system may provide at least one stimulus to the user based on the stimulus pattern. In some cases, the operations of this step may refer to, or be performed by, a stimulus unit as described with reference to FIG. 2.

Figure 7:
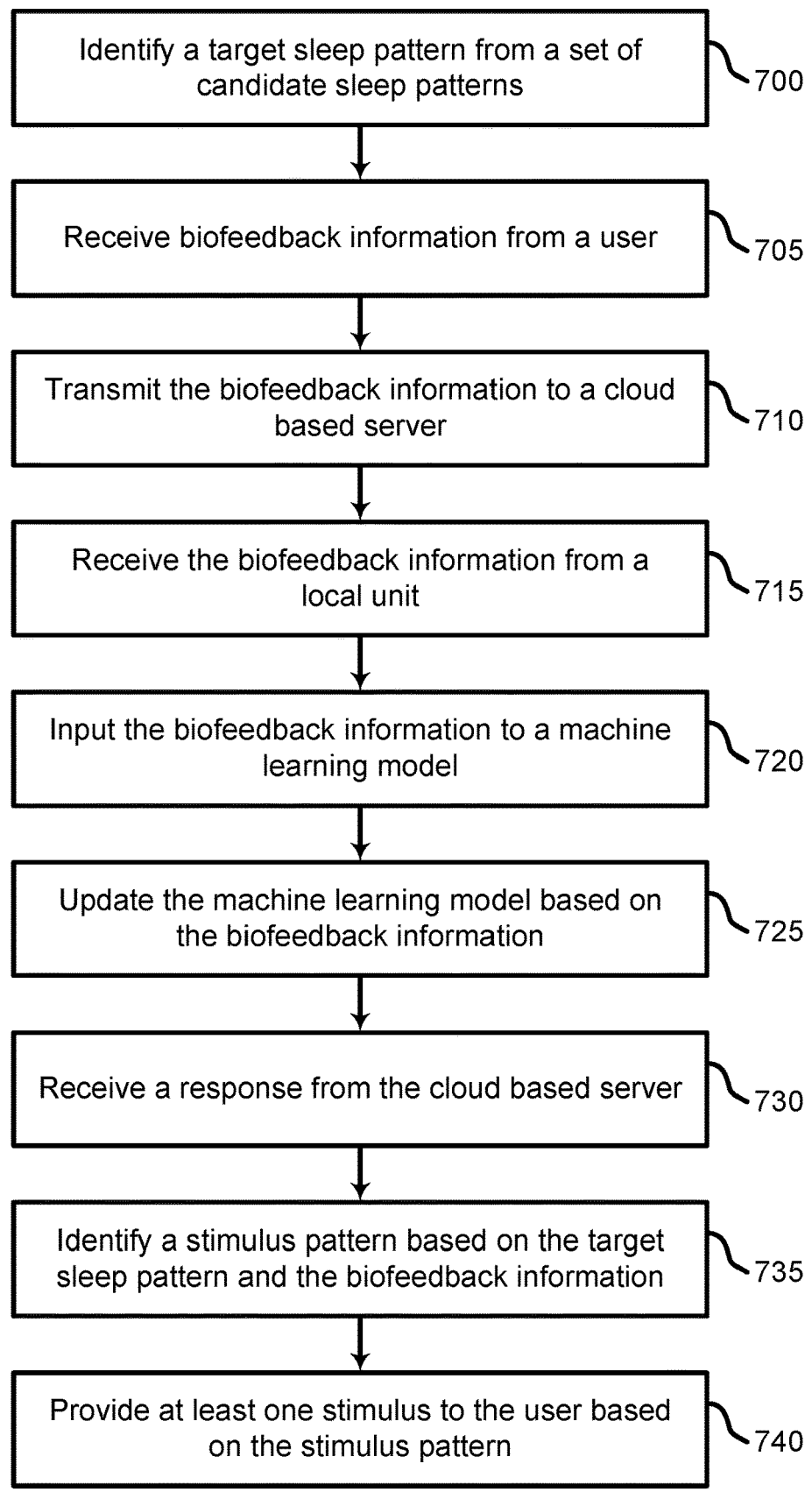

FIG. 7 shows an example of a process for modifying sleep patterns based on biofeedback in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

At step 700, the system may identify a target sleep pattern from a set of candidate sleep patterns. In some cases, the operations of this step may refer to, or be performed by, a sleep pattern unit as described with reference to FIG. 2.

At step 705, the system may receive biofeedback information from a user. In some cases, the operations of this step may refer to, or be performed by, a biofeedback unit as described with reference to FIG. 2.

At step 710, the system may transmit the biofeedback information to a cloud based server. In some cases, the operations of this step may refer to, or be performed by, a communications unit as described with reference to FIG. 2.

At step 715, the system may receive the biofeedback information from a local unit. In some cases, the operations of this step may refer to, or be performed by, a server as described with reference to FIG. 1.

At step 720, the system may input the biofeedback information to a machine learning model, where the response is based on a prediction of the machine learning model. In some cases, the operations of this step may refer to, or be performed by, a server as described with reference to FIG. 1.

At step 725, the system may update the machine learning model based on the biofeedback information. In some cases, the operations of this step may refer to, or be performed by, a server as described with reference to FIG. 1.

At step 730, the system may receive a response from the cloud based server, where the stimulus pattern is based on the response. In some cases, the operations of this step may refer to, or be performed by, a communications unit as described with reference to FIG. 2.

At step 735, the system may identify a stimulus pattern based on the target sleep pattern and the biofeedback information. In some cases, the operations of this step may refer to, or be performed by, a stimulus unit as described with reference to FIG. 2.

At step 740, the system may provide at least one stimulus to the user based on the stimulus pattern. In some cases, the operations of this step may refer to, or be performed by, a stimulus unit as described with reference to FIG. 2.

Figure 8:
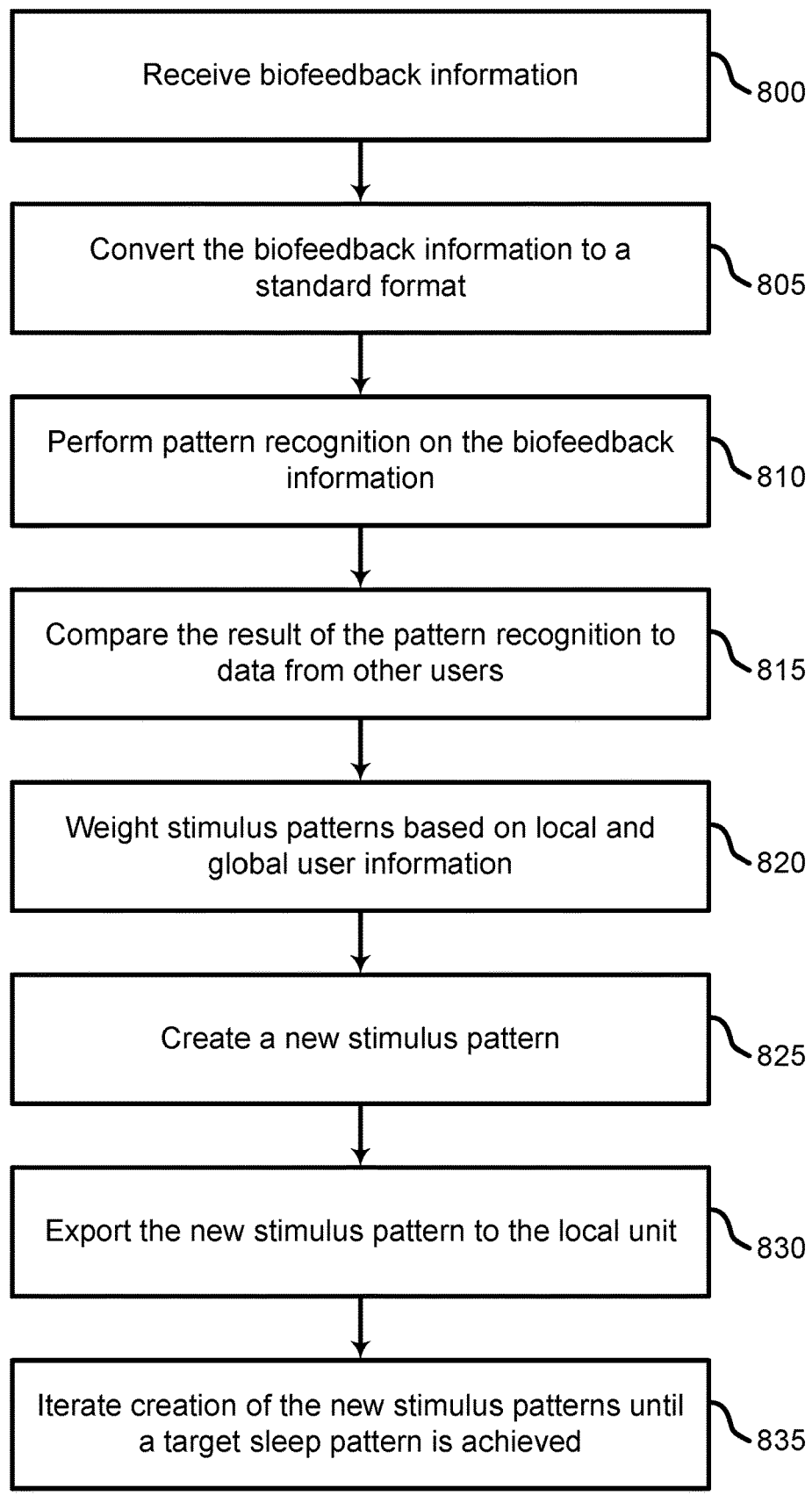

FIG. 8 shows an example of a process for modifying sleep patterns based on biofeedback in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

At step 800, the system may receive biofeedback information. At step 805, the system may convert the biofeedback information to a standard format.

At step 810, the system may perform pattern recognition on the biofeedback information. At step 815, the system may compare the result of the pattern recognition to data from other users.

At step 820, the system may weight stimulus patterns based on local and global user information. At step 825, the system may create a new stimulus pattern.

At step 830, the system may export the new stimulus pattern to the local unit. At step 835, the system may iterate creation of the new stimulus patterns until a target sleep pattern is achieved.

Thus, methods for modifying sleep patterns based on biofeedback are described. The methods may include identifying a target sleep pattern from a plurality of candidate sleep patterns, receiving biofeedback information from a user, identifying a stimulus pattern based on the target sleep pattern and the biofeedback information, and providing at least one stimulus to the user based on the stimulus pattern.

An apparatus for modifying sleep patterns based on biofeedback is also described. The apparatus may include a processor, memory in electronic communication with the processor, and instructions stored in the memory. The instructions may be operable to cause the processor to identify a target sleep pattern from a plurality of candidate sleep patterns, receive biofeedback information from a user, identify a stimulus pattern based on the target sleep pattern and the biofeedback information, and provide at least one stimulus to the user based on the stimulus pattern.

A non-transitory computer readable medium storing code for modifying sleep patterns based on biofeedback is also described. In some examples, the code comprises instructions executable by a processor to identify a target sleep pattern from a plurality of candidate sleep patterns, receive biofeedback information from a user, identify a stimulus pattern based on the target sleep pattern and the biofeedback information, and provide at least one stimulus to the user based on the stimulus pattern.

Some examples of the method, apparatus, non-transitory computer readable medium, and system described above may further include identifying a target cognitive improvement. Some examples may further include selecting the target sleep pattern based on the target cognitive improvement. Some examples may further include providing a cognitive test to the user. Some examples may further include receiving cognitive performance information based on the cognitive test, wherein the target cognitive improvement is based at least in part on the cognitive performance information. Some examples may further include providing a cognitive performance target recommendation to the user based on the cognitive performance information.

Some examples of the method, apparatus, non-transitory computer readable medium, and system described above may further include transmitting the cognitive performance information to a cloud based server. Some examples may further include receiving a response from the cloud based server, wherein the target cognitive improvement is based at least in part on the response.

Some examples of the method, apparatus, non-transitory computer readable medium, and system described above may further include receiving the cognitive performance information from a local unit. Some examples may further include inputting the cognitive performance information to a machine learning model, wherein the response is based at least in part on a prediction of the machine learning model.

Some examples of the method, apparatus, non-transitory computer readable medium, and system described above may further include providing a subsequent cognitive test to the user. Some examples may further include updating the machine learning model based on a result of the subsequent cognitive test.

Some examples of the method, apparatus, non-transitory computer readable medium, and system described above may further include receiving a cognitive improvement selection from the user, wherein the target cognitive improvement is based at least in part on the cognitive improvement selection. In some examples, the target cognitive improvement comprises a memory target, a concentration target, an energy target, an anxiety reduction target, a problem solving ability target, or any combination thereof.

Some examples of the method, apparatus, non-transitory computer readable medium, and system described above may further include transmitting the target cognitive improvement to a cloud based server. Some examples may further include receiving a response from the cloud based server, wherein the target sleep pattern is based at least in part on the response.

Some examples of the method, apparatus, non-transitory computer readable medium, and system described above may further include receiving the target cognitive improvement from a local unit. Some examples may further include inputting the target cognitive improvement to a machine learning model, wherein the response is based at least in part on a prediction of the machine learning model. In some examples, the target cognitive improvement comprises a waking cognitive performance improvement target.

Some examples of the method, apparatus, non-transitory computer readable medium, and system described above may further include identifying a target health improvement. Some examples may further include selecting the target sleep pattern based on the target health improvement.

Some examples of the method, apparatus, non-transitory computer readable medium, and system described above may further include providing a health survey to the user, wherein the target health improvement is based at least in part on the health survey. Some examples may further include identifying one or more user characteristics, wherein the target sleep pattern is identified based at least in part on the one or more user characteristics. In some examples, the one or more user characteristics comprise an age, a gender, health information, a sleep history, or any combination thereof. Some examples may further include providing a survey to the user, wherein the one or more user characteristics are based at least in part on the survey.

In some examples of the method, apparatus, non-transitory computer readable medium, and system described above, the biofeedback information comprises electroencephalogram (EEG) information, electrocardiogram (ECG) information, electromyogram (EMG) information, mechanomyogram (MMG) information, electrooculography (EOG) information, galvanic skin response (GSR) information, magnetoencephalogram (MEG) information, pulse information, breathing information, or any combination thereof.

Some examples of the method, apparatus, non-transitory computer readable medium, and system described above may further include transmitting the biofeedback information to a cloud based server. Some examples may further include receiving a response from the cloud based server, wherein the stimulus pattern is based at least in part on the response. Some examples may further include receiving the biofeedback information from a local unit. Some examples may further include inputting the biofeedback information to a machine learning model, wherein the response is based at least in part on a prediction of the machine learning model. Some examples may further include updating the machine learning model based at least in part on the biofeedback information.

In some examples of the method, apparatus, non-transitory computer readable medium, and system described above, the at least one stimulus is selected from a set of stimuli comprising sounds, lights, vapors, aromas, or any combination thereof. In some examples, the at least one stimulus comprises at least two stimuli from the set of stimuli. In some examples, the set of stimuli further comprises a haptic stimulus, a temperature stimulus, a pain stimulus, a taste stimulus or any combination thereof. In some examples, the target sleep pattern comprises a sleep pattern associated with a lucid dream state.

Some examples of the method, apparatus, non-transitory computer readable medium, and system described above may further include identifying a subsequent user activity, wherein the target sleep pattern is based at least in part on the subsequent user activity. Some examples may further include providing a sleep initiation stimulus to the user. Some examples may further include providing a waking stimulus to the user.

In some examples of the method, apparatus, non-transitory computer readable medium, and system described above, the target sleep pattern comprises a set of target sleep stages, wherein each of the target sleep stages is associated with one or more time intervals. In some examples, the set of sleep stages comprises a rapid eye movement (REM) stage, a non-REM stage, an N1 sleep stage, and N2 sleep stage, an N3 sleep stage, or any combination thereof. In some examples, the biofeedback and the at least one stimulus are provided as part of a continuous feedback loop.

The description and drawings described herein represent example configurations and do not represent all the implementations within the scope of the claims. For example, the operations and steps may be rearranged, combined or otherwise modified. Also, structures and devices may be represented in the form of block diagrams to represent the relationship between components and avoid obscuring the described concepts. Similar components or features may have the same name but may have different reference numbers corresponding to different figures.

Some modifications to the disclosure may be readily apparent to those skilled in the art, and the principles defined herein may be applied to other variations without departing from the scope of the disclosure. Thus, the disclosure is not limited to the examples and designs described herein, but is to be accorded the broadest scope consistent with the principles and novel features disclosed herein.

The described methods may be implemented or performed by devices that include a general-purpose processor, a digital signal processor (DSP), an application specific integrated circuit (ASIC), a field programmable gate array (FPGA) or other programmable logic device, discrete gate or transistor logic, discrete hardware components, or any combination thereof. A general-purpose processor may be a microprocessor, a conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). Thus, the functions described herein may be implemented in hardware or software and may be executed by a processor, firmware, or any combination thereof. If implemented in software executed by a processor, the functions may be stored in the form of instructions or code on a computer-readable medium.

Computer-readable media includes both non-transitory computer storage media and communication media including any medium that facilitates transfer of code or data. A non-transitory storage medium may be any available medium that can be accessed by a computer. For example, non-transitory computer-readable media can comprise random access memory (RAM), read-only memory (ROM), electrically erasable programmable read-only memory (EEPROM), compact disk (CD) or other optical disk storage, magnetic disk storage, or any other non-transitory medium for carrying or storing data or code.

Also, connecting components may be properly termed computer-readable media. For example, if code or data is transmitted from a website, server, or other remote source using a coaxial cable, fiber optic cable, twisted pair, digital subscriber line (DSL), or wireless technology such as infrared, radio, or microwave signals, then the coaxial cable, fiber optic cable, twisted pair, DSL, or wireless technology are included in the definition of medium. Combinations of media are also included within the scope of computer-readable media.

In this disclosure and the following claims, the word "or" indicates an inclusive list such that, for example, the list of X, Y, or Z means X or Y or Z or XY or XZ or YZ or XYZ. Also the phrase "based on" is not used to represent a closed set of conditions. For example, a step that is described as "based on condition A" may be based on both condition A and condition B. In other words, the phrase "based on" shall be construed to mean "based at least in part on."

What is claimed is:

1. A method comprising:
   identifying a target sleep pattern from a plurality of candidate sleep patterns, wherein the target sleep pattern is based at least in part on one or more time intervals associated with a set of sleep stages;
   receiving biofeedback information from a user;
   identifying a stimulus pattern based on the target sleep pattern and the biofeedback information, the stimulus pattern comprising at least one stimuli effecting at least one sleep stage of the set of sleep stages; and providing at least one stimulus to the user based on the stimulus pattern.

2. The method of claim 1, further comprising:
identifying a target cognitive improvement; and
selecting the target sleep pattern based on the target cognitive improvement.

3. The method of claim 2, further comprising:
providing a cognitive test to the user; and
receiving cognitive performance information based on the cognitive test, wherein the target cognitive improvement is based at least in part on the cognitive performance information.

4. The method of claim 3, further comprising:
transmitting the cognitive performance information to a cloud based server; and
receiving a response from the cloud based server indicating the target cognitive improvement.

5. The method of claim 4, further comprising:
receiving the cognitive performance information at a cloud based server; and
inputting the cognitive performance information to a machine learning model, wherein the response is based at least in part on a prediction of the machine learning model.

6. The method of claim 2, further comprising:
receiving a cognitive improvement selection from the user, wherein the target cognitive improvement is based at least in part on the cognitive improvement selection.

7. The method of claim 2, wherein:
the target cognitive improvement comprises a memory target, a concentration target, an attention target, an anxiety reduction target, a problem solving ability target, or any combination thereof.

8. The method of claim 2, further comprising:
transmitting the target cognitive improvement to a cloud based server; and
receiving a response from the cloud based server indicating the target sleep pattern.

9. The method of claim 8, further comprising:
receiving the target cognitive improvement at a cloud based server; and
inputting the target cognitive improvement to a machine learning model, wherein the response is based at least in part on a prediction of the machine learning model.

10. The method of claim 1, further comprising:
identifying a target health improvement; and
selecting the target sleep pattern based on the target health improvement.

11. The method of claim 10, further comprising:
providing a health survey to the user, wherein the target health improvement is based at least in part on the health survey.

12. The method of claim 1, further comprising:
identifying one or more user characteristics, wherein the target sleep pattern is identified based at least in part on the one or more user characteristics.

13. The method of claim 12, wherein:
the one or more user characteristics comprise an age, a gender, health information, a sleep history, or any combination thereof.

14. The method of claim 12, further comprising:
providing a survey to the user, wherein the one or more user characteristics are based at least in part on the survey.

15. The method of claim 1, wherein:
the biofeedback information comprises electroencephalogram (EEG) information, electrocardiogram (ECG) information, electromyogram (EMG) information, mechanomyogram (MMG) information, electrooculography (EOG) information, galvanic skin response (GSR) information, magnetoencephalogram (MEG) information, pulse information, breathing information, or any combination thereof.

16. The method of claim 1, further comprising:
transmitting the biofeedback information to a cloud based server; and
receiving a response from the cloud based server indicating the stimulus pattern.

17. The method of claim 16, further comprising:
receiving the biofeedback information at a cloud based server; and
inputting the biofeedback information to a machine learning model, wherein the response is based at least in part on a prediction of the machine learning model.

18. The method of claim 1, wherein:
the target sleep pattern comprises the set of target sleep stages, wherein each of the target sleep stages is associated with at least one time interval of the one or more time intervals.

19. The method of claim 1, wherein:
the set of sleep stages comprises a rapid eye movement (REM) stage, a non-REM stage, an N1 sleep stage, and N2 sleep stage, an N3 sleep stage, or any combination thereof.

20. An apparatus for modifying sleep patterns based on biofeedback, comprising:
a processor and a memory storing instructions and in electronic communication with the processor;
a sleep pattern unit configured to identify a target sleep pattern from a plurality of candidate sleep patterns;
a biofeedback unit configured to receive biofeedback information from a user;
a stimulus unit configured to identify a stimulus pattern based on the target sleep pattern and the biofeedback information; and
a vapor delivery unit configured to provide at least one stimulus to the user based on the stimulus pattern, wherein providing the at least one stimulus comprises at least ejecting a vapor at an angle.

* * * * *